(12) United States Patent
Corin et al.

(10) Patent No.: US 8,211,110 B1
(45) Date of Patent: Jul. 3, 2012

(54) MINIMALLY INVASIVE TOOL TO FACILITATE IMPLANTING A PEDICLE SCREW AND HOUSING

(75) Inventors: James Corin, Boulder, CO (US); Michael Fulton, Broomfield, CO (US)

(73) Assignee: Lanx, Inc., Broomfield, CO (US)

( * ) Notice: Subject to any disclaimer, the term of this patent is extended or adjusted under 35 U.S.C. 154(b) by 348 days.

(21) Appl. No.: 11/938,073

(22) Filed: Nov. 9, 2007

Related U.S. Application Data

(60) Provisional application No. 60/865,365, filed on Nov. 10, 2006.

(51) Int. Cl.
*A61B 17/70* (2006.01)
(52) U.S. Cl. .................................... 606/86 A; 606/104
(58) Field of Classification Search ............... 606/86 A, 606/279, 99, 104, 914
See application file for complete search history.

(56) References Cited

U.S. PATENT DOCUMENTS

| | | | | |
|---|---|---|---|---|
| 2,990,570 A | * | 7/1961 | Gilpatrick | 16/257 |
| 5,530,998 A | * | 7/1996 | Hurst et al. | 24/590.1 |
| 6,004,326 A | * | 12/1999 | Castro et al. | 606/99 |
| 6,183,472 B1 | | 2/2001 | Lutz | |
| 2004/0039384 A1 | * | 2/2004 | Boehm et al. | 606/61 |
| 2004/0144194 A1 | * | 7/2004 | Allen et al. | 74/512 |
| 2004/0147937 A1 | * | 7/2004 | Dunbar et al. | 606/99 |
| 2005/0065517 A1 | * | 3/2005 | Chin | 606/61 |
| 2005/0067815 A1 | * | 3/2005 | Dearden et al. | 280/728.3 |
| 2005/0131408 A1 | * | 6/2005 | Sicvol et al. | 606/61 |
| 2005/0137593 A1 | * | 6/2005 | Gray et al. | 606/61 |
| 2005/0228400 A1 | * | 10/2005 | Chao et al. | 606/104 |
| 2006/0074418 A1 | * | 4/2006 | Jackson | 606/61 |
| 2006/0074445 A1 | * | 4/2006 | Gerber et al. | 606/191 |
| 2006/0200132 A1 | * | 9/2006 | Chao et al. | 606/61 |
| 2006/0247630 A1 | * | 11/2006 | Iott et al. | 606/61 |
| 2006/0247658 A1 | * | 11/2006 | Pond et al. | 606/104 |

OTHER PUBLICATIONS

Acta Orthop Scand article dated Jun. 1984, by Bostman O. Myllynen P. Riska EB.

* cited by examiner

*Primary Examiner* — Eduardo C Robert
*Assistant Examiner* — Jerry Cumberledge
(74) *Attorney, Agent, or Firm* — Holland & Hart LLP

(57) ABSTRACT

A minimally invasive tool to facilitate implanting a pedicle screw and housing is provided. The minimally invasive tool includes a first sleeve having flexible tabs that couple to a housing and a second sleeve slidably engaged in the first sleeve. The second sleeve provides reinforcing such that the first and second sleeve provide counter torque for driving the pedicle screw.

28 Claims, 7 Drawing Sheets

MINIMALLY INVASIVE TOOL TO FACILITATE IMPLANTING A PEDICLE SCREW AND HOUSING

PRIORITY UNDER 35 USC §119

The present application claims priority to U.S. Provisional Patent Application Ser. No. 60/865,365, filed Nov. 10, 2006, titled MINIMALLY INVASIVE TOOL TO FACILITATE IMPLANTING A PEDICLE SCREW AND HOUSING, the disclosure of which is expressly incorporated herein by reference.

RELATED APPLICATION

The technology of the present application relates to U.S. patent application Ser. No. 10/915,902, titled Screw and Rod Fixation System, filed Aug. 10, 2004, which is incorporated here by reference.

FIELD OF THE INVENTION

The present invention relates to spinal fixation devices and more particularly to a pedicle screw and rod fixation assembly useful in stabilizing a spine of a patient.

BACKGROUND OF THE INVENTION

Over the years, several techniques and systems have been developed for correcting spinal injuries and/or degenerative spinal processes. Spinal correction frequently requires stabilizing a portion of the spine to facilitate fusing portions of the spine or other correction methodologies. Medical correction of this type is frequently employed for many spinal conditions, such as, for example, degenerative disc disease, scoliosis, spinal stenosis, or the like. Frequently, these corrections also require the use of implants, such as, bone grafts. Stabilizing the spine allows bone growth between vertebral bodies such that a portion of the spine is fused into a solitary unit.

Several techniques and systems have been developed for correcting and stabilizing the spine and facilitating fusion at various levels of the spine. In one type of system, a rod is disposed longitudinally along the length of the spine in the region of concern. The rod is arranged according to the anatomy and the correction desired. In this system, the rod is aligned along the spine and engages various vertebrae along its length. The rod engages, or more typically the parallel rods, engage, the spine using fixation elements, such as, anchors attached to vertebral bodies by a bone screw.

Correction frequently require aligning the rod and screw at various angles along the length of the portion of correction. In order to provide this alignment, polyaxial screws/anchors have been developed. Many variations of polyaxial screw and rod fixation systems exist on the market today. Implanting the screws, anchors, and rods as can be appreciated typically requires a relatively large incision and dissection of the skin and muscle of the patient resulting in increased recovery, surgical trauma and the like.

Accordingly, to reduce for example surgical trauma, there is a need for a screw and rod fixation system that provides a strong, effective, and secure lock of the screw and rod in the desired position and angle that can be implanted using minimally invasive systems.

BRIEF DESCRIPTION OF THE DRAWING

The accompanying drawings illustrate various embodiments of the present invention and are a part of the specification. The illustrated embodiments are merely examples and illustrations of the present invention and do not limit the scope of the invention.

DETAILED DESCRIPTION

Figure 1:
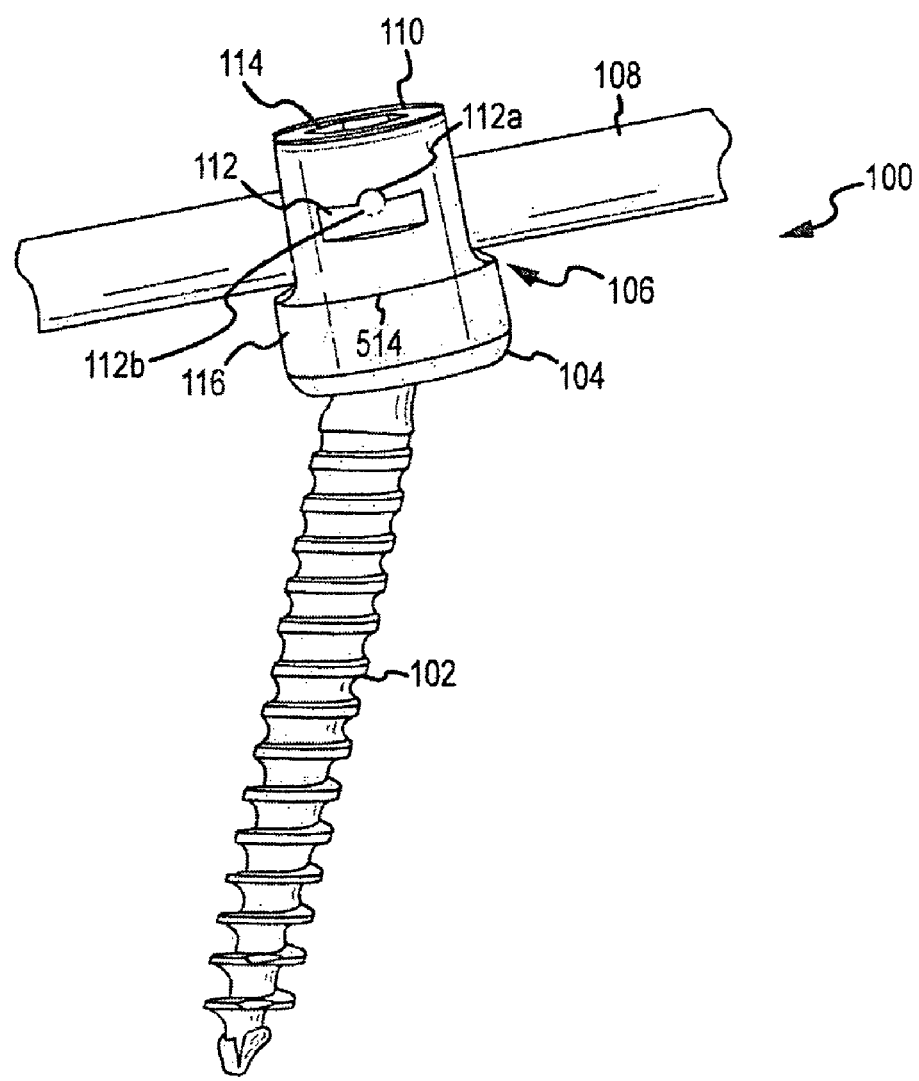
FIG. 1 shows a perspective view of a screw and rod fixation system in accordance with an embodiment of the present invention.

Referring now to FIG. 1, and in accordance with certain embodiments of the present invention, a screw and rod fixation system 100 is shown. FIG. 1 shows a perspective view of system 100. System 100 includes a bone screw 102, a housing 104 having an outer surface 106, a rod 108, and a compressive member 110, such as, a setscrew. Housing 104 may contain one or more first mating surfaces 112. First mating surfaces 112 are designed to mate with a tool (described further below). First mating surfaces 112 may include an alignment ridge 112a, which also may be a dimple, detent, protrusion, rib, or the like. Alignment ridge 112a conversely may be an alignment channel 112b as shown in phantom. Also, setscrew 110 typically has one or more second mating surface 114 to mate with a tool (not specifically shown but generally understood in the art). As shown in FIG. 1, first mating surfaces 112 are actually slots on an outer surface 106 of housing 104. While shown as slots, first mating surfaces 112 may be any number of designs including one or more dimples, hex detents, or other equivalent mechanisms as are known in the art. Second mating surface 114 is shown with a hex shape to accept a hex driver useful in threading the setscrew. Of course, one of ordinary skill in the art would recognize other and equivalent first and second mating surfaces 112, 114 are possible.

Figure 2:
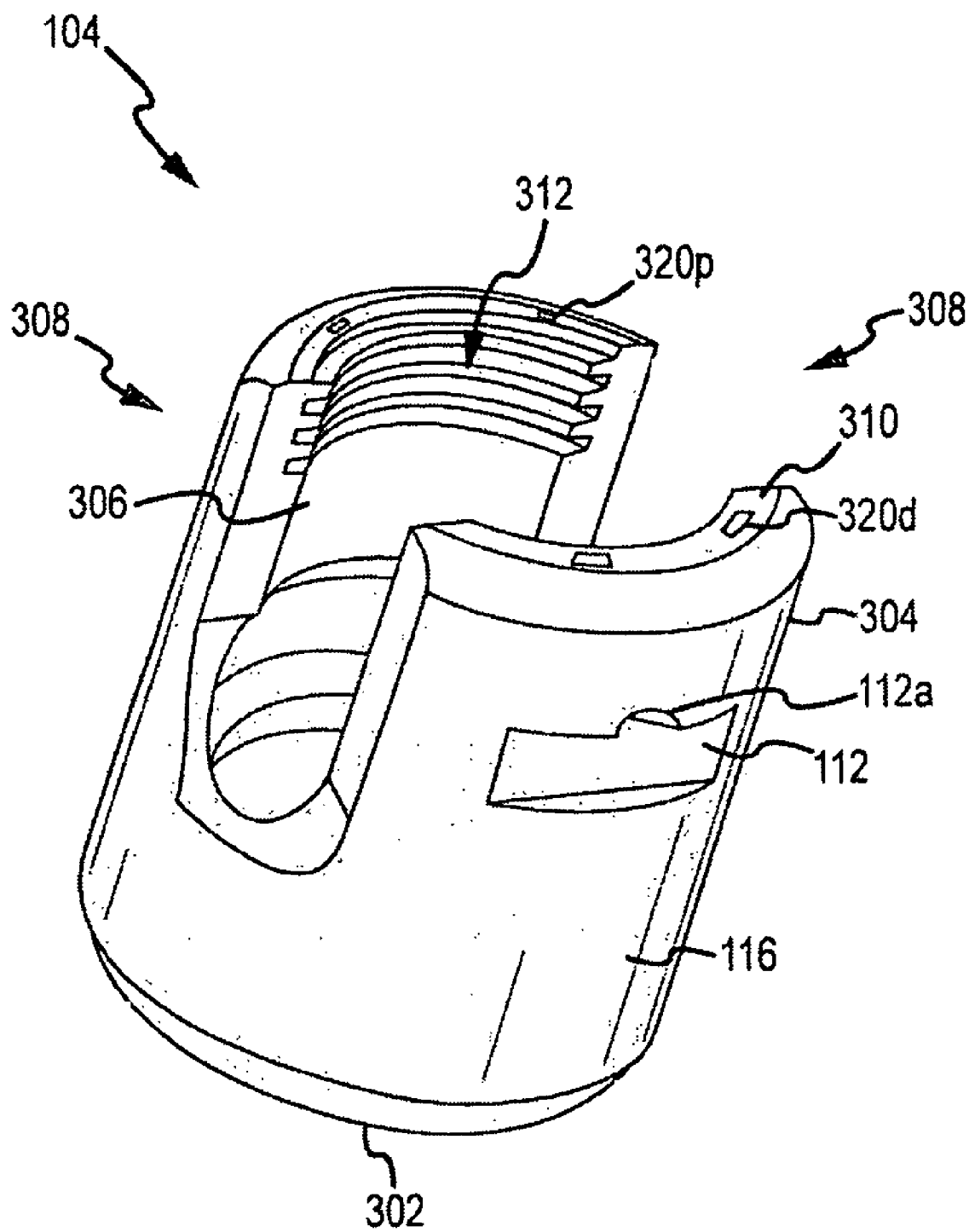
FIG. 2 shows a perspective view of a housing associated with an embodiment of the present invention shown in FIG. 1.

Referring now to FIG. 2, housing 104 is described in more detail. Housing 104 may be referred to as a coupling device, seat, or anchor. Housing 104 has a bone facing surface 302, at least one sidewall 304 having an outer surface 106 and an inner surface 306 (best seen in FIG. 2), first mating surfaces 112, a pair of opposed slots 308 in sidewall 304, a top edge 310, and a through hole 312 extending from top edge 310 to bone facing surface 302. Top edge 310 may have alignment points 320, which will be explained in more detail below. Alignment points 320 may be protrusions (as shown by 320p) or detents (as shown by 320d) as a matter of design choice, but it is believed detents would provided a lower profile.

The housing 104 is shown with one cylindrically shaped sidewall 304. It is believed providing housing 104 as a cylindrical shape reduces the profile of the device, but other shapes are possible, such as cubic or the like. If housing 104 had multiple sidewalls 304, the edges between the multiple sides, should be beveled or rounded to inhibit tissue trauma.

Figure 3:
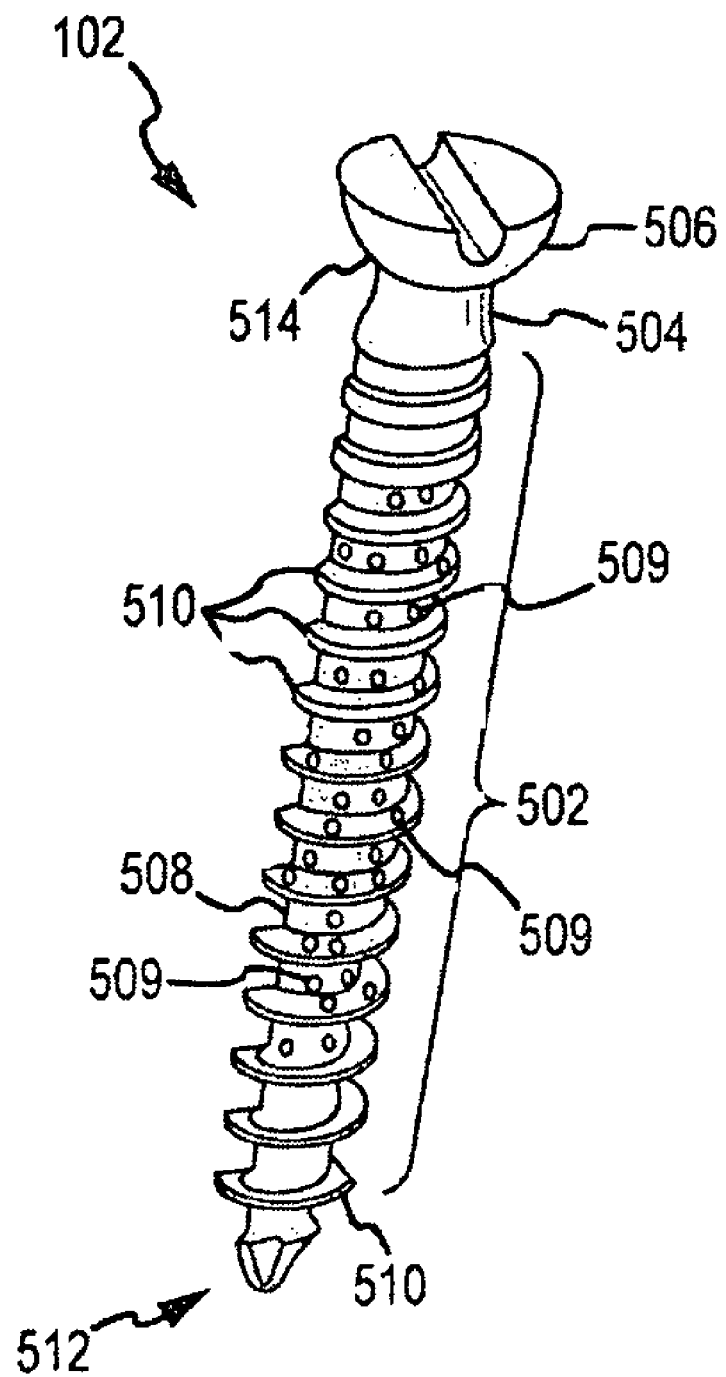
FIG. 3 shows a perspective view of a bone screw associated with an embodiment of the present invention shown in FIG. 1.
Figure 4:
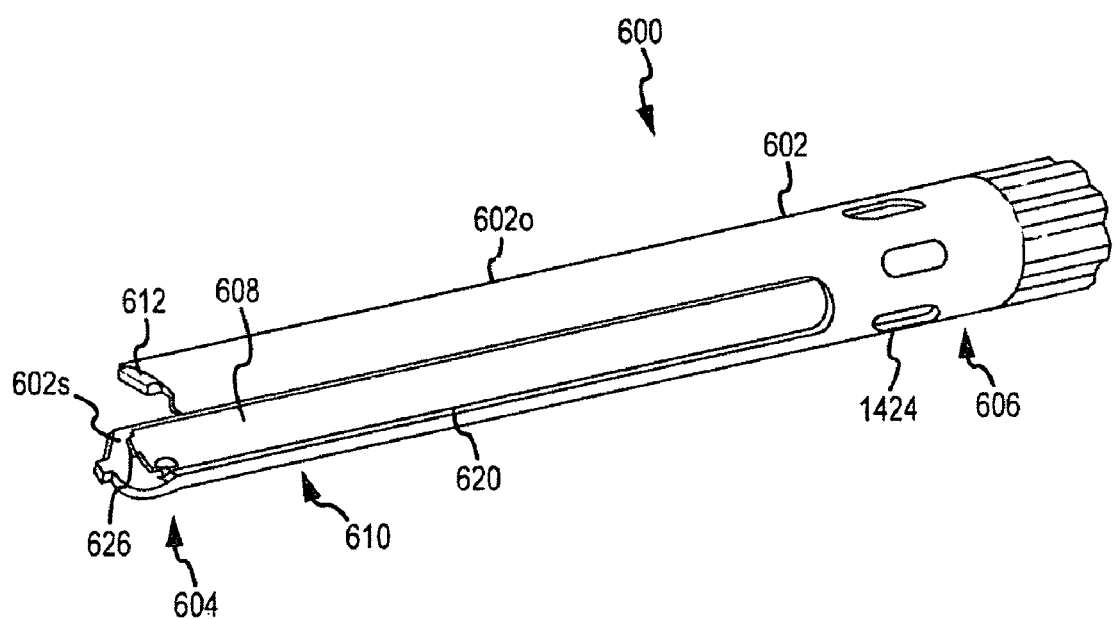
FIGS. 4-7 show a tool useful for implanting the screw and rod system.
Figure 5:
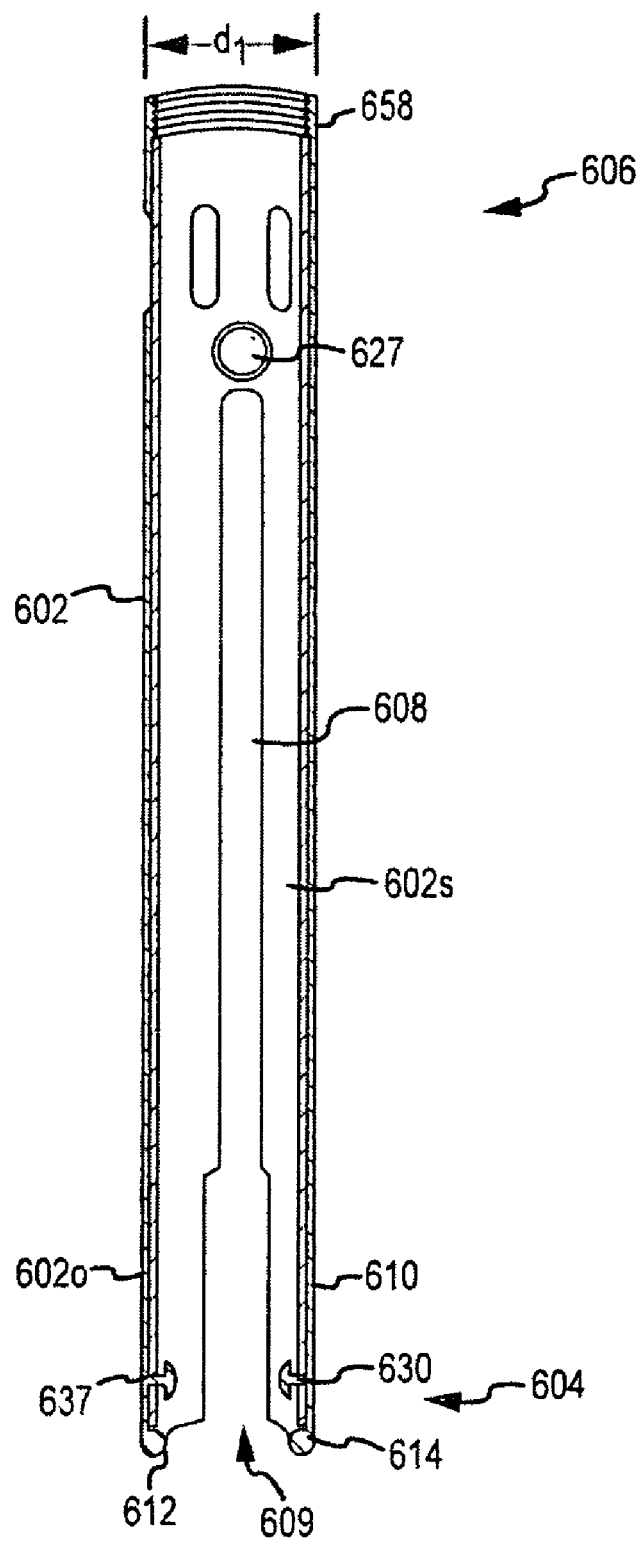
Figure 6:
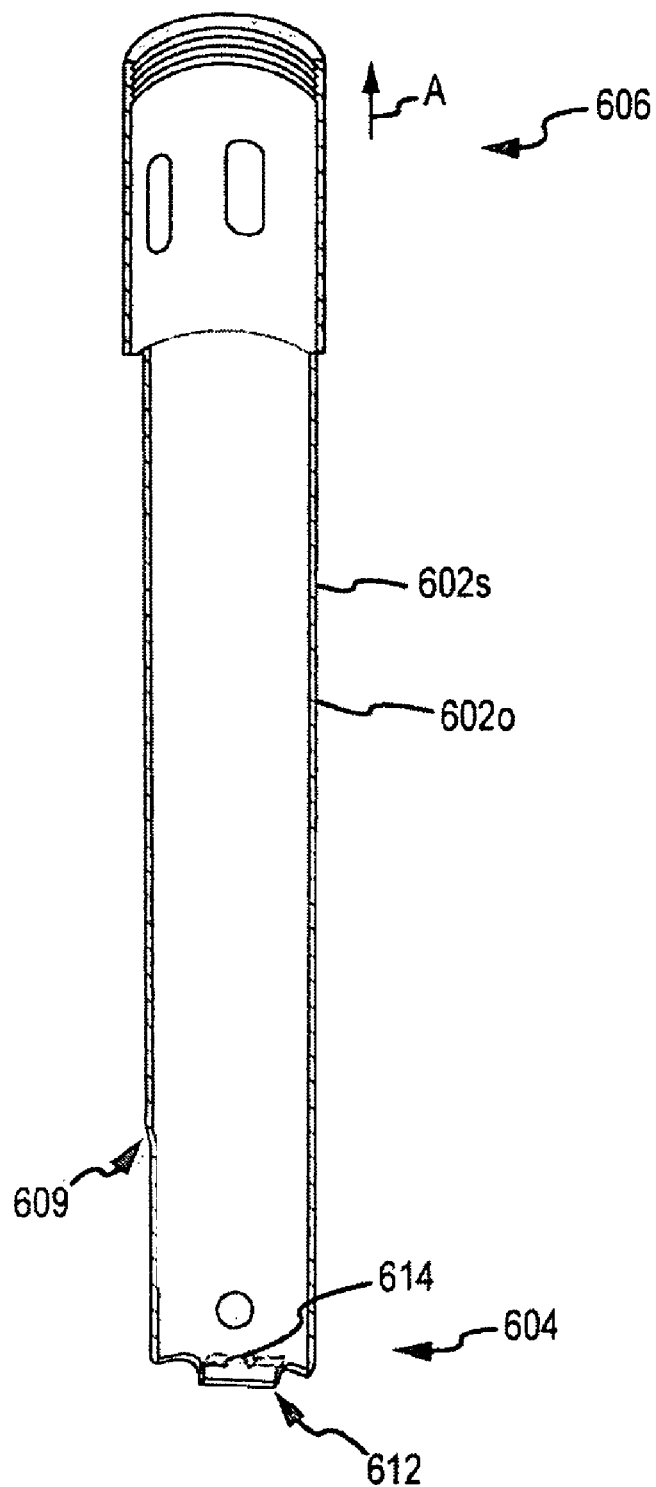
Figure 7:
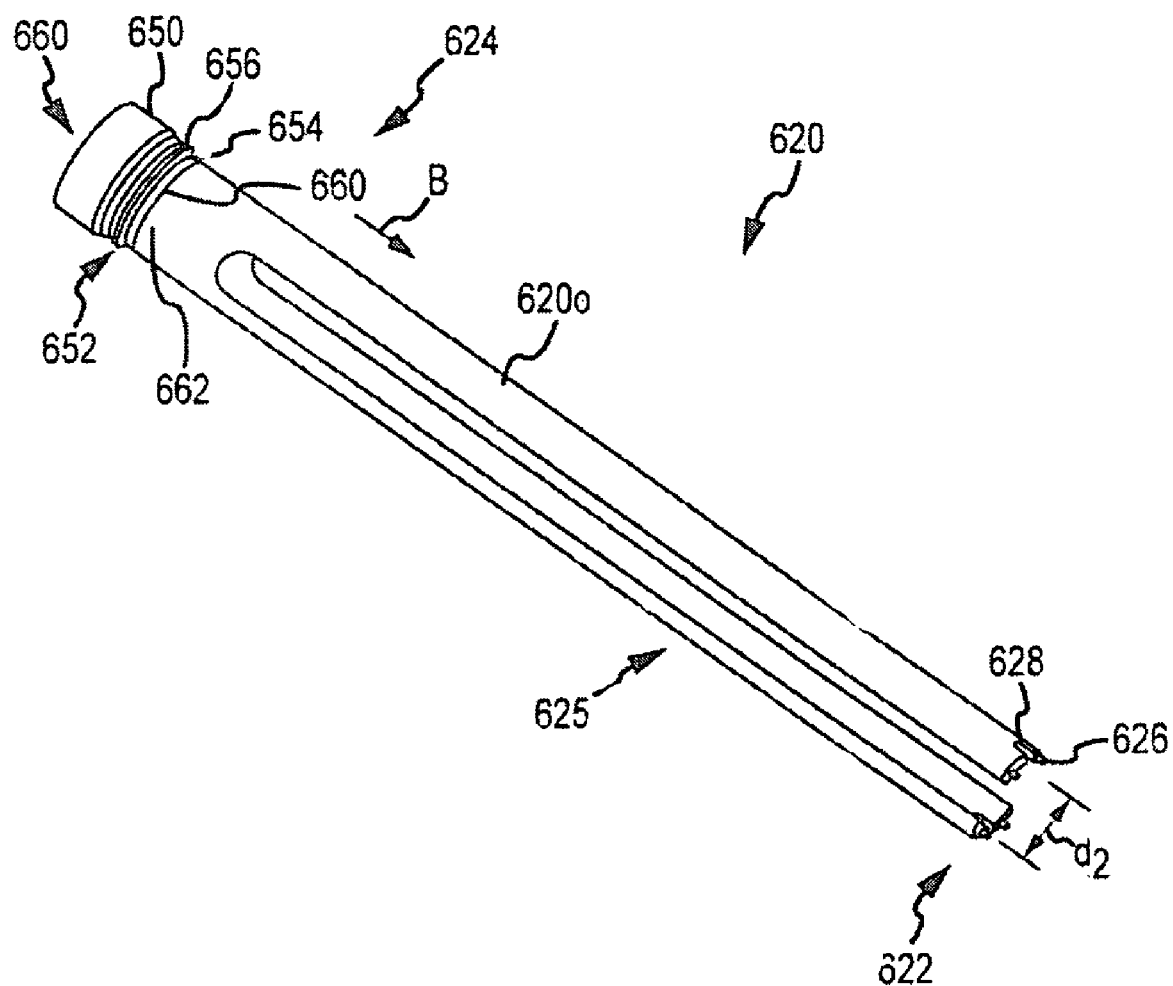

Bone screw 102 will now be described with reference to FIG. 3. While a particular bone screw 102 is described for completeness, any conventional bone screw is usable with the technology of the present invention. Bone screw 102 has a threaded portion 502, a transition portion 504, and a head portion 506. Threaded portion 502 can use any conventional thread, but as shown, threaded portion 502 has a shaft 508 and threads 510 machined such that shaft 508 has an increasing diameter from the tip 512 to transition portion 504. Further, threads 510 become relatively thicker towards transition portion 504. Designing threaded portion 502 in this fashion increases the frictional engagement of bone screw 102 in bone and generally increases the screw strength. To facilitate fusion between screw 102 and the bone, bone growth channels 509 may be provided in shaft 508, thread 510, or a combination thereof. It is believed micro-channels 509 in thread 510 facilitates bone growth and fusion of the screw to bone.

Transition portion 504 comprises the portion of bone screw 102 between threaded portion 502 and head portion 506. Transition portion 504 could be integrated into threaded portion 502. Transition portion 504 may be straight, curved, bowed, flared, or the like to transition threaded portion 502 to head portion 506.

Head 506 is shown with a convex outer surface 514 to cooperatively engage a corresponding concave surface in housing 104, not specifically shown by generally understood in the art. The convex outer surface 514 being designed to cooperatively engage the concave surface in housing 104 allows for polyaxial orientation of bone screw 102 with respect to housing 104. Head 506 is shown as a conventional flat head screw with a slot 516 to receive a tool, such as a screw driver. Rotation of the tool while engaged with slot 516 drive bone screw 102 into the associated bone. While shown as a flat head having a convex outer surface, other conventional bone screws are possible as are generally known in the art, such as, for example, heads with a more spherical shape, heads with a hex driver mating surface, heads with a fixed orientation with respect to housing 104, or the like.

Referring now to FIGS. 4-8, a tool 600 is provided to facilitate implanting the above described screws and rods. Tool 600 would typically be inserted through the skin of a patient after sufficient dilation. Tool 600 comprises a series of sleeves that will be explained in turn. Tool 600 includes a first, outer sleeve 602, sometimes referred to as first or outer. First sleeve 602 has an inner surface 602s and an outer surface 602o. Inner surface 602s defines a first sleeve diameter d1. First sleeve 602 includes a distal end 604 releasably connectable to housing 104 at first mating surfaces 112, as will be explained further below. First sleeve 602 has a proximate end 606 residing external to the patient. Extending from distal end 604 towards proximate end 606 are slots 608 separating tabs 610. Slots 608 include a flared portion 609. Flared portion 609 increases the flexibility or elasticity of tabs 610, which is useful in connecting first sleeve 602 to housing 104. Tabs 610 include first tool mating surface 612 to engage first mating surfaces 112 on housing 104. Rotating first sleeve 602 causes housing 104 to cause tabs 610 to expand. As first sleeve 602 is rotated, first tool mating surfaces 612, which are shown as protrusions, slide into first mating surfaces 112, which are shown as detents or grooves. Flexible tabs 610 collapse towards each other allowing outer sleeve 602 to grip housing 104 when first tool mating surface 612 align with first mating surfaces 112. First mating surface 612 optionally may be provided with an alignment dimple 614 to mate with alignment ridge 112a.

A second or inner sleeve 620 is provided to slidingly engage outer sleeve 602. Second sleeve 620 has a second outer surface 620o defining a second diameter d2 which is less than d1 and allows second sleeve to fit inside first sleeve in a sliding relation. Second sleeve 620 comprises distal end 622 and proximate end 624. Distal end 622 includes alignment portions 626 (which may be protrusions 626p (as shown) to mate with alignment detents 320d or which may be alignment detents 626d to mate with alignment protrusions 320p). Alignment portion 626 mate with corresponding alignment points 320 along top edge 310 of housing 104.

Second sleeve 620 includes at least one, but as shown two, alignment channels 628. Alignment channels 628 are shown opposite each other but could be otherwise configured. First sleeve 602 has at least one, but as shown two, corresponding alignment tabs 630 attached to an inner surface 602s. Alignment channel(s) 628 and alignment tab(s) 630 are matched such that when second sleeve 620 is slidably received in first sleeve 602, alignment tab(s) 630 move along and engage alignment slot(s) 628 to facilitate mating alignment portion 626 with alignment point 320. Second sleeve 620, optionally, may include one or more alignment tracks 625. Alignment tracks 625 fittingly engage with alignment ridge 627 (shown in FIG. 5) to facilitate alignment points 320 aligning with alignment portions 626 and alignment channels 628 aligning with alignment tabs 630.

Once slid into place second sleeve is rotationally locked to housing 104 by alignment, portions 626 and alignment points 320 and rotationally locked to the first sleeve by alignment channels 628 and alignment tabs 630. Thus, second sleeve 620 acts as a strengthening member to inhibit torque from causing first sleeve 602 to twist off of housing 104 while driving, for example, bone screw into bone. To, facilitate the connection, pin alignment tabs 630 may have a flared surface 637. Moreover, alignment channels 628 may be, tapered to pinch or grasp tabs 630.

Once second sleeve 620 is slidably inserted into first sleeve 602, a connector 650 couples the proximate ends of the sleeves 602 and 620 together. In this exemplary embodiment, connector 650 causes first sleeve 602 and second sleeve 620 to clamp and lock to housing 104. For example, connector 650 may have a shaft 652 with outer surface 654 having threads 656. Inner surface 602s of first sleeve 602 at the proximate end would have corresponding threads 658. Shaft 652 would have a pushing surface 660 that abuts a proximate edge 662 of second sleeve 620. Threading connector 650 onto corresponding threads 658 pulls first sleeve 602 in direction A and pushes second sleeve in a direction B, opposite direction A by causing pushing surface 660 to push down on proximate edge 662. The relative forces between first sleeve 602 and second sleeve 620 clamps first sleeve 602 and second 620 to housing 104. In this exemplary embodiment, first tool mating surface 612 applies a force against first mating surfaces 112 in direction A and the distal edge of second sleeve 620 applies a force against top edge 310 of housing 104 providing a clamping force. Connector 650 may have a tool mating surface 660 to allow a tool to thread the connector 650 to and from first sleeve 602.

Once connected, a bone screw driver can be inserted through second sleeve 620 to thread bone screw 102 into the bone. First and second sleeve 602 and 620 provide counter torque to allow driving the screw.

While the invention has been particularly shown and described with reference to an embodiment thereof, it will be understood by those skilled in the art that various other changes in the form and details may be made without departing from the spirit and scope of the invention.

We claim:

1. A tool for facilitating minimally invasive surgical procedures, the tool comprising:
   a first sleeve, the first sleeve comprising:
      a distal end having a distal tip, and a proximate end opposite the distal end,
      an inner surface and an outer surface, the inner surface defining a first diameter, a plurality of tabs elastically attached to the distal end of the first sleeve,
a plurality of first slots in the distal end of the first sleeve separating the plurality of tabs,
a mating surface on at least one of the plurality of tabs, wherein the mating surface is adapted to engage a corresponding mating surface on a housing, and
at least one protrusion coupled to the inner surface proximate the distal tip and projecting radially inwardly,
a second sleeve, the second sleeve comprising:
a distal end having a distal tip and a proximate end opposite the distal end,
an inner surface and an outer surface, the outer surface defining a second diameter less than the first diameter,
at least one channel at the distal end proximate the distal tip corresponding to the at least one protrusion;
wherein the at least one protrusion and the at least one channel are configured to selectively lock with one another;
a connector adapted to couple the proximate end of the first sleeve with the proximate end of the second sleeve, wherein the outer surface of the second sleeve is slidingly engaged with the inner surface of the first sleeve such that the at least one protrusion proximate the distal tip of the first sleeve fits in the corresponding at least one channel proximate the distal tip of the second sleeve, wherein the second sleeve is slidably inserted in the first sleeve until the at least one protrusion fits in the corresponding at least one channel and inhibits the elasticity and rotational movement of the plurality of tabs.

2. The tool according to claim 1 wherein the at least one protrusion comprises an alignment tab having a flared surface.

3. The tool according to claim 1 wherein the at least one channel comprises a tapered channel to engage the corresponding at least one protrusion.

4. The tool according to claim 1 wherein the first sleeve is adapted to rotationally lock relative to the second sleeve when the at least one protrusion is disposed in the corresponding at least one channel.

5. The tool according to claim 1 wherein the connector is a threaded connector adapted to threadedly couple the proximate end of the first sleeve to the proximate, end of the second sleeve.

6. The tool according to claim 5 wherein the at least one protrusion is adapted to be further drawn into the at least one channel when the first and second sleeves are threadedly coupled.

7. The tool according to claim 1 wherein the first sleeve inner surface further comprises an alignment ridge adapted to engage an alignment track disposed in the second sleeve.

8. The tool according to claim 7 wherein the second sleeve is adapted to be slidably received within the first sleeve when the alignment ridge is aligned with the alignment track.

9. The tool according to claim 1 wherein the first sleeve distal end comprises an alignment member adapted to engage an alignment feature in the housing of a pedicle screw.

10. The tool according to claim 9 wherein the alignment member comprises an alignment dimple.

11. The tool according to claim 1 wherein the second sleeve distal end comprises an alignment portion adapted to engage corresponding alignment points on a housing of a polyaxial screw.

12. The tool according to claim 11 wherein the alignment portion comprises at least one pin member adapted to engage a detent in the housing.

13. The tool according to claim 11 wherein the alignment portion is adapted to engage a protrusion on the housing extending.

14. The tool according to claim 1 wherein the first and second sleeve distal ends are adapted to engage the housing of a polyaxial screw, and wherein the first sleeve is restricted from rotational and axial movement relative to the housing when the at least one protrusion is disposed in the corresponding at least one channel.

15. A tool for facilitating minimally invasive surgical procedures, the tool comprising:
a first elongate sleeve having inner and outer surfaces, a proximal end and a distal end, the inner surface defining a first diameter, the inner surface having a protrusion extending therefrom proximate the distal end, at least a first mating surface proximate the distal end of the first elongate sleeve adapted to engage a corresponding mating surface in a spinal implant;
a second elongate sleeve having inner and outer surfaces, a proximal end and a distal end, the outer surface defining a second diameter smaller than the first diameter, the outer surface having a channel adapted to receive the protrusion when the second sleeve is slidably disposed within the first sleeve, at least an alignment portion proximate the distal end of the second elongate sleeve adapted to engage a corresponding alignment portion in the spinal implant;
wherein the at least one protrusion and the at feast one channel are configured to selectively lock with one another;
an alignment member coupled to the first elongate sleeve inner surface and adapted to be received within an alignment track disposed in the second elongate sleeve outer surface, the alignment member and alignment track positioned to allow the second elongate sleeve to be slidably received within the first elongate sleeve in an orientation which generally aligns the protrusion with the channel.

16. The tool according to claim 15 wherein the elasticity and rotational movement of the distal ends of the first and second sleeves is restricted when the protrusion is disposed in the channel.

17. The tool according to claim 16 wherein the protrusion extends from the first sleeve with a narrow portion widening to a bulbously-shaped head.

18. The tool according to claim 15 further comprising a pedicle screw having an elongate threaded member and a head adapted to cooperatively engage the housing member that is adapted to receive a rod.

19. The tool according to claim 15 wherein the the first mating surface at the distal end of first sleeve is adapted to couple to an outer surface of the housing, and the alignment portion at the distal end of the second sleeve is adapted to couple to an upper edge of the housing, when the protrusion is disposed within the channel.

20. A tool for facilitating minimally invasive surgical procedures, the tool comprising:
a first elongate sleeve having inner and outer surfaces, a proximal end and a distal end, the inner surface defining a first diameter, the inner surface having a protrusion extending therefrom proximate the distal end;
a second elongate sleeve having inner and outer surfaces, a proximal end and a distal end, the outer surface defining a second diameter smaller than the first diameter, the outer surface having a channel adapted to receive the protrusion when the second sleeve is slidably disposed within the first sleeve;

an alignment member coupled to the first elongate sleeve inner surface and adapted to be received within an alignment track disposed in the second elongate sleeve, the alignment member and alignment track positioned to allow the second elongate sleeve to be slidably received within the first elongate sleeve in an orientation which generally aligns the protrusion with the channel, wherein the at least one protrusion and the at least one channel are configured to selectively lock with one another; and a first mating surface proximate the distal end of the first elongate sleeve and a second mating surface proximate the distal end of the second elongate sleeve, wherein the first and second mating surfaces are adapted to engage a spinal implant to releasably secure the first and second sleeves to the spinal implant.

21. The tool as in claim 20 wherein the protrusion extends radially inward from the first sleeve inner surface.

22. The tool as in claim 20 wherein the alignment track comprises an elongated slot extending from the distal end of the second sleeve towards the proximal end of the second sleeve.

23. The tool as in claim 22 wherein the elongated slot has a length greater than one-half the length of the second sleeve.

24. The tool as in claim 22 wherein the first sleeve comprises an elongated slot that extends from the first sleeve distal end towards the first sleeve proximal end, and wherein the first sleeve elongated slot is generally aligned with the second sleeve elongated slot when the second sleeve and first sleeve are selectively locked together.

25. The tool as in claim 20 wherein the spinal implant comprises a pedicle screw, and wherein the first and second sleeve are adapted to engage a housing portion of the pedicle screw.

26. The tool as in claim 25 wherein the housing portion of the pedicle screw is adapted to receive an elongated rod.

27. The tool as in claim 25 wherein the first sleeve distal end is adapted to engage a first surface of the housing portion and the second sleeve distal end is adapted to engage a second surface of the housing portion to releasably secure the first and second sleeves to the housing portion.

28. The tool as in claim 20 wherein the first sleeve further comprises a second protrusion and the second sleeve further comprises a second channel, and wherein the second protusion and second channel are configured to selectively lock with one another.

* * * * *